United States Patent
Sakanishi

(10) Patent No.: US 8,258,091 B2
(45) Date of Patent: Sep. 4, 2012

(54) OIL COMPOSITION AND CLEANSING COSMETIC CONTAINING THE OIL COMPOSITION

(75) Inventor: Yuichi Sakanishi, Ohtake (JP)

(73) Assignee: Daicel Chemical Industries, Ltd., Osaka (JP)

( * ) Notice: Subject to any disclaimer, the term of this patent is extended or adjusted under 35 U.S.C. 154(b) by 17 days.

(21) Appl. No.: 12/554,565

(22) Filed: Sep. 4, 2009

(65) Prior Publication Data

US 2010/0062960 A1 Mar. 11, 2010

(30) Foreign Application Priority Data

Sep. 10, 2008 (JP) ................................ 2008-232021

(51) Int. Cl.
*A61Q 1/14* (2006.01)
(52) U.S. Cl. ..................................................... 510/136
(58) Field of Classification Search .................. 510/277, 510/435, 136
See application file for complete search history.

(56) References Cited

U.S. PATENT DOCUMENTS

| | | | | |
|---|---|---|---|---|
| 5,500,451 A | * | 3/1996 | Goldman et al. | 521/64 |
| 6,613,338 B1 | * | 9/2003 | Schreiber et al. | 424/401 |
| 2004/0197276 A1 | | 10/2004 | Takase et al. | |
| 2005/0118210 A1 | * | 6/2005 | Kachi et al. | 424/401 |
| 2005/0180942 A1 | * | 8/2005 | Shimizu et al. | 424/70.31 |
| 2005/0271610 A1 | * | 12/2005 | Neuss et al. | 424/65 |
| 2008/0300429 A1 | * | 12/2008 | Sakanishi et al. | 568/680 |

FOREIGN PATENT DOCUMENTS

| | | |
|---|---|---|
| JP | 2004-75589 A | 3/2004 |
| JP | 2006-347896 A | 12/2006 |
| WO | WO-03/035015 A1 | 5/2003 |
| WO | WO2006025226 * | 9/2006 |

* cited by examiner

*Primary Examiner* — David W Wu
*Assistant Examiner* — Thuy-Ai Nguyen
(74) *Attorney, Agent, or Firm* — Birch, Stewart, Kolasch & Birch, LLP

(57) ABSTRACT

An oil composition contains 1 to 50 percent by weight of a glycerol monoether compound represented by following Formula (1):

$$R^1O\text{—}(C_3H_6O_2)_{n1}\text{—}H \qquad (1)$$

wherein $R^1$ represents an alkyl or alkenyl group which may be substituted, and "n1" denotes a number of repeating glycerol units ranging from 1 to 3; and 1 to 50 percent by weight of a polyglycerol monoether compound represented by following Formula (2):

$$R^2O\text{—}(C_3H_6O_2)_{n2}\text{—}H \qquad (2)$$

wherein $R^2$ represents an alkyl or alkenyl group which may be substituted, and "n2" denotes a number of repeating glycerol units ranging from 4 to 20. The oil composition is usable as a foamable cleansing agent that is mild to the skin, exhibits superior detergency for removing oily cosmetics, and is usable even when the skin is wet.

5 Claims, No Drawings

OIL COMPOSITION AND CLEANSING COSMETIC CONTAINING THE OIL COMPOSITION

BACKGROUND OF THE INVENTION

1. Field of the Invention

The present invention relates to oil compositions useful typically as cleansing agents for removing oily cosmetics. More specifically, it relates to oil compositions which contain a glycerol monoalkyl ether and/or a diglycerol monoalkyl ether in combination with a polyglycerol monoalkyl ether, thereby have superior detergency, are usable under a wide range of conditions, can wash well, and can stably form fine foams.

2. Description of the Related Art

Cleansing agents for removing cosmetics (make-ups) are roughly classified as oil, gel, and foamable cleansing agents. Oil and gel cleansing agents generally require massaging by fingers so as to satisfactorily mix with cosmetics and to remove the cosmetics. The massaging applies a pressure to the skin, and this often damages the skin. In addition, these agents cause sticky feeling upon use and are not readily rinsable. In contrast, foamable cleansing agents are less irritating to the skin, excel in feel upon use, and have thereby been desirably used as cleansing agents.

Known foamable cleansing agents include those containing a foamable aerosol composition that includes an oil-in-water (O/W) emulsion including two phases, i.e., n aqueous phase and an inner oily phase. The inner oily phase contains a propellant dissolved therein, and the aqueous phase has poor compatibility or miscibility with the propellant. However, cleansing agents using a foamable aerosol composition of an oil-in-water (O/W) emulsion are not appropriate as detergents for oily cosmetics, because they contain an aqueous phase as a continuous phase and thereby have poor miscibility with, and poor detergency to, oily cosmetics. Known foamable cleansing agents having improved detergency to oily cosmetics include water-in-oil (W/O) compositions for constituting oily foamable aerosols, which contain a polyoxyethylene-added nonionic surfactant, an alkyl phosphate derivative, and a polyglycerol fatty acid ester, respectively (see Japanese Unexamined Patent Application Publication (JP-A) No. 2004-75589; PCT International Publication Number WO 2003/035015; and Japanese Unexamined Patent Application Publication (JP-A) No. 2006-347896). These water-in-oil (W/O) compositions for oily foamable aerosols, however, often suffer from phase transition from a water-in-oil (W/O) phase to an oil-in-water (O/W) phase upon cleansing of cosmetics and are difficult to use when used under wet conditions (when the skin is wet). Additionally, they have still insufficient detergency.

SUMMARY OF THE INVENTION

Accordingly, an object of the present invention is to provide an oil composition which is usable as a foamable cleansing cosmetic mild to the skin, which exhibits superior detergency to oily cosmetics, and which is usable even when the skin is wet.

After intensive investigations to achieve the object, the present inventors have found that an oil composition containing a specific glycerol monoether compound and a specific polyglycerol monoether compound can form fine foams and, when used as a cleansing agent for removing oily cosmetics, can sufficiently remove the oily cosmetics without applying a strain on the skin. They have also found that the oil composition has superior solubility or miscibility with both an aqueous phase and an oily phase, can thereby maintain a single-phase state over a wide range even where an aqueous phase and an oily phase are present as a mixture, can exhibit superior detergency even when the skin is wet, and can wash well. The present invention has been made based on these findings and further investigations.

Specifically the present invention provides, in an embodiment, an oil composition which includes 1 to 50 percent by weight of one or more glycerol monoether compounds represented by following Formula (1):

$$R^1O\text{—}(C_3H_6O_2)_{n1}\text{—}H \tag{1}$$

wherein $R^1$ represents an alkyl or alkenyl group which may be substituted; and "n1" denotes a number of repeating glycerol units ranging from 1 to 3; and 1 to 50 percent by weight of one or more polyglycerol monoether compounds represented by following Formula (2):

$$R^2O\text{—}(C_3H_6O_2)_{n2}\text{—}H \tag{2}$$

wherein $R^2$ represents an alkyl or alkenyl group which may be substituted; and "n2" denotes a number of repeating glycerol units ranging from 4 to 20.

The oil composition preferably further contains 50 to 98 percent by weight of at least one selected from the group consisting of silicone oils, ester oils, and triacylglycerols.

In another embodiment, the present invention provides a cleansing cosmetic containing the oil composition.

The oil composition according to the present invention contains a specific glycerol monoether compound and a specific polyglycerol monoether compound, thereby shows superior solubility or miscibility with both an aqueous phase and an oily phase, can maintain a single-phase state over a broad range even when such an aqueous phase and an oily phase are present as a mixture, and can exhibit superior detergency even when the skin is wet. The oil composition is free from sticky feel upon use, can stably form fine foams, and is readily rinsable (removable). The oil composition, when used as a cleansing agent for removing oily cosmetics, can remove and wash the oily cosmetics well without applying a strain on the skin.

When the oil composition is charged with a propellant into a tightly sealed container while being pressurized, a press of the spray button allows a mixture of the oil composition and the propellant to be discharged at a single blow, and the propellant abruptly expands due to pressure reduction to thereby allow the oil composition to form very fine foams. Thus, it is advantageously usable as a skin-friendly foamable cleansing cosmetic.

These and other objects, features, and advantages of the present invention will be understood more fully from the following description of the preferred embodiments. All numbers are herein assumed to be modified by the term "about."

DESCRIPTION OF THE PREFERRED EMBODIMENTS

Oil Compositions

Oil compositions according to embodiments of the present invention contain 1 to 50 percent by weight of one or more glycerol monoether compounds represented by following Formula (1):

$$R^1O\text{—}(C_3H_6O_2)_{n1}\text{—}H \tag{1}$$

wherein $R^1$ represents an alkyl or alkenyl group which may be substituted, and "n1" denotes a number of repeating glycerol units ranging from 1 to 3; and 1 to 50 percent by weight of one or more polyglycerol monoether compounds represented by following Formula (2):

wherein $R^2$ represents an alkyl or alkenyl group which may be substituted; and "n2" denotes a number of repeating glycerol units ranging from 4 to 20.

Glycerol Monoether Compounds

Glycerol monoether compounds for use herein are represented by following Formula (1):

$$R^1O\text{---}(C_3H_6O_2)_{n1}\text{---}H \quad (1)$$

wherein $R^1$ represents an alkyl or alkenyl group which may be substituted; and "n1" denotes a number of repeating glycerol units ranging from 1 to 3.

The repeating unit $C_3H_6O_2$ in the parentheses in Formula (1) has both structures of following Formulae (3) and (4):

$$\text{---}CH_2\text{---}CHOH\text{---}CH_2O\text{---} \quad (3)$$

$$\text{---}CH(CH_2OH)CH_2O\text{---} \quad (4)$$

$R^1$ represents an alkyl or alkenyl group which may be substituted. Exemplary alkyl groups as $R^1$ include linear alkyl groups containing about 1 to about 25 carbon atoms, such as methyl, ethyl, propyl, butyl, pentyl, hexyl, octyl, nonyl, decyl, undecyl, dodecyl, tridecyl, tetradecyl, myristyl, pentadecyl, cetyl, heptadecyl, stearyl, and behenyl groups, of which those containing about 10 to about 25 carbon atoms are preferred, and those containing about 11 to about 22 carbon atoms are more preferred; and branched-chain alkyl groups containing about 3 to about 25 carbon atoms, such as isopropyl, isobutyl, s-butyl, t-butyl, butyloctyl, isomyristyl, isocetyl, hexyldecyl, isostearyl, isobehenyl, octyldecyl, octyldodecyl, and isobehenyl groups, of which those containing about 10 to about 25 carbon atoms are preferred, those containing about 12 to about 25 carbon atoms are more preferred, and those containing about 12 to about 22 carbon atoms are especially preferred.

Exemplary alkenyl groups as $R^1$ include alkenyl groups containing about 2 to about 25 carbon atoms, such as vinyl, allyl, 1-butenyl, oleyl, linoleyl, and linolenyl groups, of which those containing about 10 to about 25 carbon atoms are preferred, those containing about 12 to about 25 carbon atoms are more preferred, and those containing about 12 to about 22 carbon atoms are especially preferred.

The alkyl groups and alkenyl groups may each have one or more of substituents. Exemplary substituents include halogen atoms, oxo groups, hydroxyl groups, substituted oxy groups (e.g., alkoxy groups, aryloxy groups, aralkyloxy groups, and acyloxy groups), carboxyl groups, substituted oxycarbonyl groups (e.g., alkoxycarbonyl groups, aryloxycarbonyl groups, and aralkyloxycarbonyl groups), substituted or unsubstituted carbamoyl groups, cyano groups, nitro groups, substituted or unsubstituted amino groups, sulfo groups, and heterocyclic groups. The hydroxyl group and carboxyl group may each be protected by a protecting group commonly used in organic syntheses. Preferred substituents which the alkyl groups and alkenyl groups as $R^1$s may have are hydroxyl groups.

Of glycerol monoether compounds of Formula (1), preferred for use herein are glycerol monoalkyl ether compounds in which $R^1$ is an alkyl or alkenyl group containing about 12 to 25 carbon atoms, such as a branched-chain alkyl group containing about 12 to about 25 carbon atoms (e.g., hexyldecyl or octyldodecyl group) or an alkenyl group containing about 12 to about 25 carbon atoms (e.g., oleyl group). Such compounds are capable of satisfactorily forming a bicontinuous structure. Each of different glycerol monoether compounds can be used alone or in combination.

The number "n1" of repeating glycerol units in glycerol monoether compounds of Formula (1) has a molecular weight distribution and ranges from 1 to 3. If the number "n1" of repeating glycerol units exceeds the above-specified range, it becomes difficult to form a bicontinuous structure, because the curvature is biased to positive.

Such glycerol monoether compounds of Formula (1), in which the number "n1" of repeating glycerol units has the molecular weight distribution, can be obtained by using, alone or in combination, each of corresponding glycerol monoether compounds represented by following Formula (5):

$$R^1O\text{---}(C_3H_6O_2)_{n3}\text{---}H \quad (5)$$

wherein $R^1$ is as defined above; and "n3" denotes a number of repeating glycerol units ranging from 1 to 1.6; and corresponding diglycerol monoether compounds represented by following Formula (6):

$$R^1\text{---}(C_3H_6O_2)_{n4}\text{---}H \quad (6)$$

wherein $R^1$ is as defined above; and "n4" denotes a number of repeating glycerol units ranging from 1.7 to 3.

For example, a glycerol monoether compound of Formula (1), in which $R^1$ is dodecyl group, and having a desired number of repeating glycerol units can be obtained by using, alone or in combination, each of glycerol monoether compounds (glycerol monododecyl ethers) of Formula (5) in which $R^1$ is dodecyl group and diglycerol monoether compounds (diglycerol monododecyl ethers) of Formula (6) in which $R^1$ is dodecyl group.

Glycerol monoether compounds of Formula (5) and diglycerol monoether compounds of Formula (6) can be prepared according to a procedure not especially limited. For example, they can be prepared by reacting an aliphatic alcohol with glycidol in the presence of a basic catalyst, so that the molar ratio of the aliphatic alcohol to glycidol falls into a specific value; by reacting a polyglycerol with an α-olefin epoxide; or by opening the ring of an alkyl glycidyl ether using a polyglycerol in the presence of an acid catalyst or alkaline catalyst.

Polyglycerol Monoether Compounds

Polyglycerol monoether compounds for use herein are represented by following Formula (2):

$$R^2O\text{---}(C_3H_6O_2)_{n2}\text{---}H \quad (2)$$

wherein $R^2$ represents an alkyl or alkenyl group which may be substituted; and "n2" denotes a number of repeating glycerol units ranging from 4 to 20.

The repeating unit $C_3H_6O_2$ in the parentheses in Formula (2) has both structures of Formulae (3) and (4). Examples of alkyl groups and alkenyl groups as $R^2$, which may be substituted, are as with the exemplified alkyl groups and alkenyl groups as $R^1$ which may be substituted.

The number "n2" of repeating glycerol units in polyglycerol monoether compounds of Formula (2) has a molecular weight distribution and ranges from 4 to 20, preferably from 4 to 15, and especially preferably from 10 to 15. A compound, if having a number "n2" of repeating glycerol units of less than 4, may have insufficient solubility in water, and, if having a number "n2" of repeating glycerol units of more than 20, may have an excessively high viscosity.

Of polyglycerol monoether compounds of Formula (2), preferred for use herein are polyglycerol monoalkyl ether compounds in which $R^1$ is an alkyl or alkenyl group containing about 12 to 25 carbon atoms, such as a branched-chain alkyl group containing about 12 to about 25 carbon atoms (e.g., hexyldecyl or octyldodecyl group) or an alkenyl group containing about 12 to about 25 carbon atoms (e.g., oleyl group). Such compounds are capable of satisfactorily forming a bicontinuous structure. Each of different polyglycerol monoether compounds can be used alone or in combination.

Polyglycerol monoether compounds of Formula (2) can be prepared according to a procedure not especially limited. For example, they can be prepared by reacting an aliphatic alcohol with glycidol in the presence of a basic catalyst, so that the molar ratio of the aliphatic alcohol to glycidol falls into a specific value; by reacting a polyglycerol with an α-olefin epoxide; or by opening the ring of an alkyl glycidyl ether using a polyglycerol in the presence of an acid catalyst or alkaline catalyst.

Oil compositions according to embodiments of the present invention essentially contain at least one glycerol monoether compound of Formula (1) and at least one polyglycerol monoether compound of Formula (2). An oil composition, if not satisfying these conditions, does not exhibit superior solubility in or miscibility with both an aqueous phase and an oily phase, does not satisfactorily maintain a single-phase state, and thereby does not exhibit superior detergency when the skin is wet.

The content of glycerol monoether compounds of Formula (1) in the oil composition is from 1 to 50 percent by weight, and is preferably from 10 to 50 percent by weight for further satisfactory detergency and for forming further stable foams. The content of polyglycerol monoether compounds of Formula (2) is from 1 to 50 percent by weight, and is preferably from 1 to 25 percent by weight for further satisfactory feel upon use and further superior economic efficiency.

Glycerol monoether compounds of Formula (1) and polyglycerol monoether compounds of Formula (2) are preferably mixed so as to have a hydrophile-lipophile balance (HLB) of around 10, for example, from about 9 to about 11, and preferably from about 9.5 to about 10.5. The hydrophile-lypophile balance (HLB) is a value indicating the balance between hydrophilicity and lipophilicity of surfactants. As used herein a "hydrophile-lipophile balance (HLB)" refers to a value calculated according to the following equation from an "organic value" and an "inorganic value" determined by the organic conception diagram.

HLB=(Inorganic value)/(Organic value)×10

The HLB can be controlled by suitably selecting combinations of the types of $R^1$ and $R^2$ and of the numbers "n1" and "n2" of repeating glycerol units in Formulae (1) and (2).

Fats and Oils

An oil composition according to a preferred embodiment of the present invention further contains one or more fats or oils, in addition to the glycerol monoether compounds of Formula (1) and the polyglycerol monoether compounds of Formula (2). Fats and oils for use herein can be any fats and oils that are in a liquid state during foaming and can be either natural fats and oils or synthetic fats and oils. Such fats and oils, if added, help to form stable foams.

Exemplary fats and oils include liquid fats and oils such as avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, perilla oil, soybean oil, peanut oil, tea oil, kaya oil, rice bran oil, Chinese wood oil, Japanese wood oil (Japanese tung oil), jojoba oil, germ oil, glycerol trioctanoate, and glycerol triisopalmitate; hydrocarbons such as liquid paraffin, squalene, squalane, and pristane; higher alcohol fatty acids such as oleic acid, tall oil fatty acids, and isostearic acid; higher alcohols such as lauryl alcohol, oleyl alcohol, isostearyl alcohol, and octyldodecanol; silicone oils such as methylpolysiloxane, methylphenylpolysiloxane, methylhydrogenpolysiloxane, and decamethylpolysiloxane; ester oils such as isopropyl myristate, isopropyl palmitate, hexyl laurate, oleyl oleate, decyl oleate, octyldodecyl myristate, hexyldecyl dimethyloctanoate, diethyl phthalate, and dibutyl phthalate; and triacylglycerols such as tripalmitoylglycerol, 1-palmitoyl-2,3-oleoylglycerol, 1,3-oleoyl-2-palmitoylglycerol, 1-palmitoleoyl-2-stearoyl-3-inoleoylglycerol, 1-linoleoyl-2-palmitoleoyl-3-stearoylglycerol. Such fats and oils for use herein also include those obtained by subjecting the above fats and oils to a treatment such as hydrogenation or separation. The fats and oils may contain an unsaturated fatty acid, a side-chain fatty acid, a diglyceride, a monoglyceride, and other glyceride components, as long as the amount thereof is trivial.

Of fats and oils, preferred are one or more fats and oils selected from silicone oils, ester oils, and triacylglycerols, for more satisfactory detergency.

The amount of fats and oils can be set without limitation and is, for example, from about 50 to about 98 percent by weight, and preferably from about 30 to about 95 percent by weight, of the total amount of the oil composition.

Oil compositions according to embodiments of the present invention may further contain other components according to necessity, as long as the objects of the present invention can be achieved. Exemplary other components include water; polyols; nonionic surfactants other than the glycerol monoether compounds and polyglycerol monoether compounds; anionic surfactants; amphoteric surfactants; lower alcohols; powders; antioxidants; antioxidation assistants; ultraviolet-absorbers; humectants; antiphlogistic agents; preservatives; pH adjusters; extracts derived from animals, vegetables, fishes/shellfishes, and microorganisms; and flavors.

Water for use herein can be either hard water or soft water. Exemplary waters include industrial water, tap water, ion-exchanged water, and distilled water. The amount of water may be adjusted according to the purpose of use and is generally from about 1 to about 50 percent by weight, and preferably from about 2 to about 20 percent by weight, of the total amount of the oil composition.

The polyols serve to destroy the liquid crystal structure of the polyglycerol monoalkyl (or monoalkenyl)ether, and the addition thereof helps the fat or oil component and water component to be dissolved in dramatically increased amounts, to improve the feel upon use and foamability.

Exemplary polyols include glycerol, diglycerol, ethylene glycol, diethylene glycol, propylene glycol, polyethylene glycol, 1,3-butylene glycol, isoprene glycol, sorbitol, sorbitan, maltitol, trehalose, xylitol, glucose, erythritol, pentaerythritol, neopentyl glycol, sucrose, mannitol, gluconic acid, dipropylene glycol, hexylene glycol, and polyphenols.

Among them, glycerol, maltitol, 1,3-butylene glycol, propylene glycol, and sorbitol are preferably used alone or in combination. These components can more satisfactorily destroy the liquid crystal structure and further improve the feel upon use and foamability. The content of polyols is, for example, from about 1 to about 40 percent by weight, and preferably from about 5 to about 30 percent by weight, of the total amount of the oil composition.

The nonionic surfactants other than the glycerol monoether compounds and polyglycerol monoether compounds are not especially limited, as long as being surfactants having no ionizable group as a hydrophilic group. Examples thereof include glycerol fatty acid esters, polyglycerol fatty acid esters, polyalkylene glycol fatty acid esters, sorbitan fatty acid esters, sugar fatty acid esters, pentaerythritol fatty acid esters, polyoxyalkylene hydrogenated castor oil fatty acid esters, fatty acid alkanolamides, polyoxyalkylene glycols, esters between a polyoxyalkylene glycol and a monohydric or polyhydric alcohol, polyoxyalkylene sugar ethers, condensates between a fatty amide and a polyoxyalkylene glycol, condensates between an aliphatic amine and a polyoxyalkylene glycol, and alkyl or alkenyl polyglycosides.

Exemplary anionic surfactants include, but are not specifically limited to, polyoxyethylene alkyl ether sulfate salts, alkyl sulfate salts, alkylbenzenesulfonate salts, as olefinsulfonate salts, glutamic acid and other amino acid surfactants, N-acylmethyltaurine salts, and alkyl phosphate salts.

Exemplary amphoteric surfactants include, but are not specifically limited to, carboxybetaine-, imidazolinium-, sulfobetaine-, and alanine-type amphoteric surfactants.

Exemplary lower alcohols include, but are not specifically limited to, ethanol and propyl alcohol.

The powders (powdery components) are not especially limited and include inorganic powders and organic powders. Exemplary inorganic powders include talc, kaolin, mica, sericite, muscovite, phlogopite, synthetic mica, lepidolite, biotite, lithia mica, vermiculite, magnesium carbonate, zirconium silicate, aluminum silicate, barium silicate, calcium silicate, zinc silicate, magnesium silicate, strontium silicate, metal tungstates, magnesium, silica, zeolite, barium sulfate, calcined calcium sulfate (calcined gypsum), calcium phosphate, fluoroapatite, hydroxyapatite, ceramic powders, activated carbon, medical carbon (medical charcoal), metal soaps (e.g., zinc myristate, calcium palmitate, and aluminum stearate), and boron nitride, Exemplary organic powders include polyamide powders (nylon powders), polyethylene powders, poly(methyl methacrylate) powders, polystyrene powders, powders of styrene-acrylic acid copolymers, benzoguanamine resin powders, and cellulose powders.

Exemplary antioxidants include, but are not specifically limited to, vitamin E, dibutylhydroxytoluene, butylhydroxyanisole, and gallic acid esters.

Exemplary antioxidation assistants include, but are not specifically limited to, ascorbic acid, phytic acid, kephalin, and maleic acid.

Exemplary ultraviolet-absorbers include, but are not specifically limited to, benzophenone derivatives such as 2 hydroxy-4-methoxybenzophenone, 2-hydroxy-4-methoxybenzophenone-5-sulfonic acid, salts of 2-hydroxy-4-methoxybenzophenone-5-sulfonic acid, and dihydroxydimethoxybenzophenone; p-aminobenzoic acid and derivatives thereof, such as ethyl p-aminobenzoate; methoxycinnamic acid derivatives such as ethyl p-methoxycinnamate, isopropyl p-methoxycinnamate, and octyl p-methoxycinnamate; salicylic acid derivatives such as octyl salicylate and phenyl salicylate; urocanic acid and derivatives thereof; 4-tert-butyl-4'-methoxydibenzoylmethane; 2-(hydroxy-5'-methylphenyl)benzotriazole; and methyl o-aminobenzoate (methyl anthranilate).

Exemplary humectants include, but are not specifically limited to, sodium lactate, pyrrolidonecarboxylic acid and salts thereof.

Exemplary antiphlogistic agents include, but are not specifically limited to, glycyrrhizic acid and derivatives thereof, glycyrrhetic acid and derivatives thereof, allantoin, hydrocortisone acetate, and azulene.

Exemplary preservatives include, but are not specifically limited to, methylparaben (methyl p-hydroxybenzoate), propylparaben (propyl p-hydroxybenzoate), and phenoxyethanol.

Exemplary pH adjusters include, but are not specifically limited to, citric acid, hydrochloric acid, sulfuric acid, phosphoric acid, sodium hydroxide, and ammonia.

Exemplary extracts derived from animals, vegetables (plants), fishes/shellfishes, and microorganisms include, but are not specifically limited to, extracts such as tea extract, aloe extract, ginkgo extract, swertia herb extract, mugwort extract, garlic extract, Scutellaria root extract, rosemary extract, sponge gourd extract, placental extract, extract from lactic acid bacteria culture, and seaweed extract.

Flavors for use herein are not specifically limited, as long as being those generally used in cosmetics.

When the oil composition according to the present invention is charged together with a propellant into a hermetically sealed container while being pressurized, a press of the spray button allows a mixture of the oil composition and the propellant to be discharged at a single blow, and the propellant abruptly expands due to pressure reduction to thereby allow the oil composition to form very fine foams.

Exemplary propellants for use herein include chlorofluorocarbons such as trichlorofluoromethane, dichlorodifluoromethane, dichlorofluoromethane, trichlorotrifluoroethane, and dichlorotetrafluoroethane; liquefied gases such as propane, isobutane, isopentane, n-butane, and liquefied petroleum gas. Each of different propellants can be used alone or in combination. Each of these propellants may be used in combination with dimethyl ether, carbon dioxide gas, and/or nitrogen gas.

The amount of propellants is, for example, preferably from about 2 to about 90 percent by weight, to the total amount of the oil composition. A propellant, if its amount is less than 2 percent by weight, may not sufficiently help the composition to form satisfactory foams.

Oil compositions according to embodiments of the present invention are usable typically as detergents for removing oil stains, cleansing cosmetics for removing oily cosmetics, suntan oils, baby oils, hair oils, and foamy massage oils, and, above all, are advantageously usable as cleansing cosmetics typically for removing oily cosmetics.

EXAMPLES

The present invention will be illustrated in further detail with reference to several examples below. It should be noted, however, these examples are never intended to limit the scope of the present invention.

Examples 1 to 5 and Comparative Examples 1 to 3

A series of oil compositions was prepared by mixing raw material in proportions (by weight) given in Table 1, stirring and dissolving them at 80° C., and cooling to ambient temperature (25° C.).

Next, 18 g of each of the oil compositions was charged into a 100-mL aerosol can, a valve was set, and 2 g of liquefied petroleum gas as a propellant was charged, to give a series of aerosols.

The prepared oil compositions and aerosols were evaluated in the following manner. The results are shown in Table 1. The symbol "n" in Table 1 denotes a number of repeating glycerol units (average number of repeating glycerol units) in glycerol monoether compounds and polyglycerol monoether compounds.

[Phase Condition Test]

Each 1 g of the oil compositions prepared from the examples and comparative examples was taken by dry hand or by wet hand (wet with water), the liquid phase was visually observed, and the phase condition was evaluated according to the following criteria.

Criteria:
The liquid phase was transparent: Good
The liquid phase was translucent (turbid): Poor

[Foamability Test]

Each of the aerosols prepared from the examples and comparative examples was sprayed for 2 seconds, the resulting foams were visually observed, and the foamability was evaluated according to the following criteria.

Criteria:
Very uniform and fine foams were formed: Excellent
Uniform and fine foams were formed: Good
Coarse foams were formed: Fair 2. Detergency Test Under Water-wetted Condition A lipstick (trade name "Maquillage Superior Rouge RD759", supplied by Shiseido Co., Ltd.) (0.2 g) was applied to the forearm; the applied portion of the forearm was wetted with water; about 0.5 g of each of the aerosols prepared from the examples and comparative examples was taken in the hand and sufficiently mixed with the lipstick by massaging the applied portion thirty times. How the applied lipstick was removed after massaging was visually observed, and the detergency of the aerosol compositions was evaluated according to the following criteria.

Criteria:
The lipstick was completely removed: Excellent
Almost all of the lipstick was removed: Good
The lipstick slightly remained: Fair
Almost no lipstick was removed: Poor

TABLE 1

|  |  |  | Examples | | | | | Comparative Examples | | |
| --- | --- | --- | --- | --- | --- | --- | --- | --- | --- | --- |
|  |  |  | 1 | 2 | 3 | 4 | 5 | 1 | 2 | 3 |
| Materials | Octyldodecyl myristate | | 65 | 65 | 65 | 65 | 65 | 65 | 65 | 65 |
|  | Glycerol oleyl ether (n = 1) | | 15 | | | | | | | |
|  | Diglycerol oleyl ether (n = 2) | | | 15 | 15 | 15 | 15 | 30 | | |
|  | Decaglycerol hexyldecyl ether (n = 10) | | | | 15 | 5 | 10 | | 30 | |
|  | Heptaglycerol octyldodecyl ether (n = 7) | | 15 | 15 | | 10 | 5 | | | 30 |
|  | Water | | 5 | 5 | 5 | 5 | 5 | 5 | 5 | 5 |
| Evaluations | Phase condition | Under dry condition | Good | Good | Good | Good | Good | Good | Good | Good |
|  |  | Under wet condition | Good | Good | Good | Good | Good | Poor | Poor | Poor |
|  | Foamability | | Excellent | Excellent | Excellent | Excellent | Excellent | Good | Fair | Good |
|  | Foam stability | | Good | Excellent | Excellent | Excellent | Good | Fair | Fair | Good |
|  | Detergency | Under dry condition | Excellent | Excellent | Excellent | Excellent | Excellent | Excellent | Excellent | Excellent |
|  |  | Under wet condition | Excellent | Excellent | Excellent | Excellent | Good | Good | Fair | Poor |

The sprayed aerosol did not form foams but remained as a liquid: Poor

[Foam Stability Test]

Each of the aerosols prepared from the examples and comparative examples was sprayed for 2 seconds, and the persistency of the resulting foams was evaluated according to the following criteria, in which the term "foam persisting time" refers to a time period within which the total volume of the foams decreased to 90% or less of the volume of foams immediately after spraying.

Criteria:
The foam persisting time was 1 minute or longer: Excellent
The foam persisting time was 30 seconds or longer but shorter than 1 minute: Good
The foam persisting time was 10 seconds or longer but shorter than 30 seconds: Fair
The sprayed aerosol did not form foams but remained as a liquid: Poor

[Detergency Test]

1. Detergency Test Under Dry Condition

A lipstick (trade name "Maquillage Superior Rouge RD759", supplied by Shiseido Co., Ltd.) (0.2 g) was applied to the forearm; about 0.5 g of each of the aerosols prepared from the examples and comparative examples was taken in the hand and sufficiently mixed with the lipstick by massaging the applied portion thirty times. How the applied lipstick was removed after massaging was visually observed, and the detergency of the aerosol compositions was evaluated according to criteria mentioned below.

While the above description is of the preferred embodiments of the present invention, it should be appreciated that the invention may be modified, altered, or varied without deviating from the scope and fair meaning of the following claims.

What is claimed is:

1. An oil composition comprising:

1 to 15 percent by weight of one or more glycerol monoether compounds represented by following Formula (1):

$$R^1O-(C_3H_6O_2)_{n1}-H \qquad (1)$$

wherein $R^1$ is an oleyl or linoleyl group; and "n1" denotes a number of repeating glycerol units ranging from 1 to 3;

5 to 25 percent by weight of one or more polyglycerol monoether compounds represented by following Formula (2):

$$R^2O-(C_3H_6O_2)_{n2}-H \qquad (2)$$

wherein $R^2$ is a butyloctyl, hexyldecyl, isostearyl, or octyldodecyl group; and "n2" denotes a number of repeating glycerol units ranging from 4 to 20;

50 to 95 percent by weight of at least one selected from the group consisting of silicone oils, ester oils, and triacylglycerols; and 2 to 20 percent by weight of water.

2. A cleansing cosmetic comprising the oil composition of claim 1.

3. The oil composition according to claim 1, wherein the content of one or more glycerol monoether compounds represented by Formula (1) is 10 to 15 percent by weight.

4. The oil composition according to claim 1, wherein n1 denotes a number of repeating glycerol units ranging from 1 to 1.6.

5. The oil composition according to claim 1, wherein the repeating unit $C_3H_6O_2$ in the parentheses in Formula (1) and (2) has both structures of the following Formulae (3) and (4):

$$-CH_2-CHOH-CH_2O- \qquad (3)$$

$$-CH(CH_2OH)CH_2O- \qquad (4).$$

* * * * *